(12) United States Patent
Millikin et al.

(10) Patent No.: US 11,591,307 B1
(45) Date of Patent: Feb. 28, 2023

(54) METHOD OF PROCESSING CANNABIS PLANT MATTER

(71) Applicants: Rory Chesley Patrick Millikin, Kelowna (CA); Matthew Kennedy, Westminster, CA (US)

(72) Inventors: Rory Chesley Patrick Millikin, Kelowna (CA); Matthew Kennedy, Westminster, CA (US)

(73) Assignee: Drive Foods Corp, Westminster, CA (US)

( * ) Notice: Subject to any disclaimer, the term of this patent is extended or adjusted under 35 U.S.C. 154(b) by 0 days.

(21) Appl. No.: 16/855,867

(22) Filed: Apr. 22, 2020

Related U.S. Application Data

(63) Continuation-in-part of application No. 16/449,338, filed on Jun. 21, 2019, now Pat. No. 10,485,373.

(60) Provisional application No. 62/691,592, filed on Jun. 28, 2018, provisional application No. 62/692,628, filed on Jun. 29, 2018, provisional application No. 62/696,670, filed on Jul. 11, 2018, provisional application No. 62/714,077, filed on Aug. 2, 2018.

(51) Int. Cl.
*A61K 36/00* (2006.01)
*C07D 311/78* (2006.01)

(52) U.S. Cl.
CPC ............... *C07D 311/78* (2013.01)

(58) Field of Classification Search
CPC ..................................... A61K 36/00
USPC ..................................... 424/725
See application file for complete search history.

(56) References Cited

U.S. PATENT DOCUMENTS

| | | | |
|---|---|---|---|
| 8,778,418 B2 * | 7/2014 | Bisterfeld Von Meer | A61K 8/9789 424/725 |
| 9,974,821 B2 * | 5/2018 | Kennedy | A61K 36/185 |
| 2016/0106705 A1 * | 4/2016 | Verzura | A61K 31/353 514/454 |

\* cited by examiner

*Primary Examiner* — Michael V Meller
(74) *Attorney, Agent, or Firm* — Christopher Pilling

(57) ABSTRACT

A method of processing cannabis plant matter is provided. It is a particular aspect of the invention to utilize cannabis waste from the processing methods and in a sense recycle and use the byproducts to create additional products. The method describes harvesting cannabis plant matter at a predetermined time, processing the cannabis plant matter to create cannabis juice and cannabis pulp, and utilizing the cannabis pulp to create additional products. This eliminates the waste from processing cannabis plant matter solving a potential crisis in the fact that cannabis plant matter having cannabinoids leech into the soil and water table from disposal.

1 Claim, 5 Drawing Sheets

METHOD OF PROCESSING CANNABIS PLANT MATTER

CROSS-REFERENCE TO RELATED APPLICATIONS

The present application is a continuation in part application to U.S. patent application Ser. No. 16/128,242, which claims priority to U.S. Provisional Application Ser. No. 62/691,592 filed on Jun. 28, 2018 entitled "A method of juicing a product via a hot and/or cold press", U.S. Provisional Application Ser. No. 62/692,628 filed on Jun. 29, 2018 entitled "A method to extract cannabinoids from products, U.S. Provisional Application Ser. No. 62/696,670 filed on Jul. 11, 2018 entitled "Systems and methods to create cannabis juice; cannabis secondary products from juicing, cannabis waste recycling; creating fertilizer from cannabis or from other cannabinoid-rich plants; remove chlorophyll, terpenes and taste from cannabis; creating cannabutter, transporting cannabis plants, trim & waste, dry & wet pet food and shampoo", and U.S. Provisional Application Ser. No. 62/714,077 filed on Aug. 2, 2018 entitled "Systems and Methods To Extract Cannabinoids from Cannabis Plant; To Remove Chlorophyll, Terpenes and/or flavor of from Cannabis Plant; to make Cannabis Oils, Butter and Tinctures, and To Recycle Cannabis Waste" the disclosure of which are hereby incorporated in their entirety at least by reference.

BACKGROUND OF THE INVENTION

1. Field of the Invention

The present invention relates to cannabis, and more particular a method of processing cannabis plant matter.

2. Description of Related Art

Cannabis as a health supplement has been practiced for over 1,000 years. Traditionally cannabis is heated to release cannabinoids, primary tetrahydrocannabinol (THC) and cannabidiol (CBD) but also emerging important cannabinoids including but not limited to tetrahydrocannabivarin THCV and cannabinol (CBN) amongst others. These cannabinoids are known to have many therapeutic and medical benefits. Additionally, cannabis in its natural form is a nutrient rich supplement comprising essential fatty acids, aminoacids, fibers, enzymes, vitamins, and minerals. Furthermore, cannabis in its natural form comprises tetrahydrocannabinol acid (THCA) and cannabidiol acid (CBDA), plus other cannabinoids including but not limited tetrahydrocannabivarin acid (THCVA), cannabinol acid (CBNA) which are non-psychoactive cannabinoids providing anti-inflammatory, neuroprotective, anti-emetic, appetite suppressant, sleep inducing, anti-proliferative amongst other medicinal properties.

BRIEF SUMMARY OF THE INVENTION

The cannabis plant matter comprises many cannabinoids in its natural state, i.e. raw, including but not limited to tetrahydrocannabinol acid (THCA), cannabidiol acid (CBDA), tetrahydrocannabivarin acid (THCVA), cannabinol acid (CBNA), cannabichromne acid (CBCA), and cannabigerolic acid (CBGA) which have many medicinal properties attributed to them. For instance, TCHA and CBDA may be used to reduce inflammation, inhibit cell growth in tumors and cancer cells, and also suppress muscle spasms. Likewise, CBCA and CBGA may be used to kill or slow bacteria growth, treat fungal infections, and release pain. THCVA may suppress appetite and CBNA may induce sleep.

It is a particular aspect of the invention to utilize cannabis waste from standard processing methods and in a sense recycle and use the byproducts from these processing methods in the method of the present invention. Despite the advantages of using the byproducts, it is a particular advantage when using cannabis plant matter. Specifically, landfills are overwhelmed and environmentalists are declaring a potential crisis in the fact that cannabis plant matter having cannabinoids leech into the soil and water table or if incinerated fill the air with cannbinoids. Thus, the present invention provides a solution to this crisis by utilizing the waste and byproducts from other the standard cannabis processing methods. In one embodiment, cannabis waste is defined as cannabis leaves, stems, small flowers that have been removed during processing, e.g. harvest and trimming. This will be described in greater detail below.

Currently, most cannabis is grown with the desired result of dried cannabis flowers, as well known in the art. This is usually a two-step process after the cannabis plant has reached maturity. First, during harvest, large fan leaves, and sometimes small leaves positioned close to the cannabis flowers are removed leaving mostly the flowers from the cannabis plant which is then hung or placed in racks to dry. After drying, the remaining leaves and visible stems are removed via trimming. Thus, the cannabis waste accumulates in each step of the two-step process. Currently, there are processes to utilize the waste from the second step process for hash, oil, cannabutter, or similar products. However, the waste from the first process is not being utilized due to the seemingly low content of cannabinoids. It is a particular advantage, that the present invention utilizes this waste.

Further, it is an aspect of the present invention to increase the cannabinoid content and strength of cannabis juice, as a majority if not all the cannabinoids after juicing cannabis end up in the pulp rather than the juice as intended. This is a problem that has been recognized by the applicant.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide a method of processing cannabis plant matter.

Figure 1:
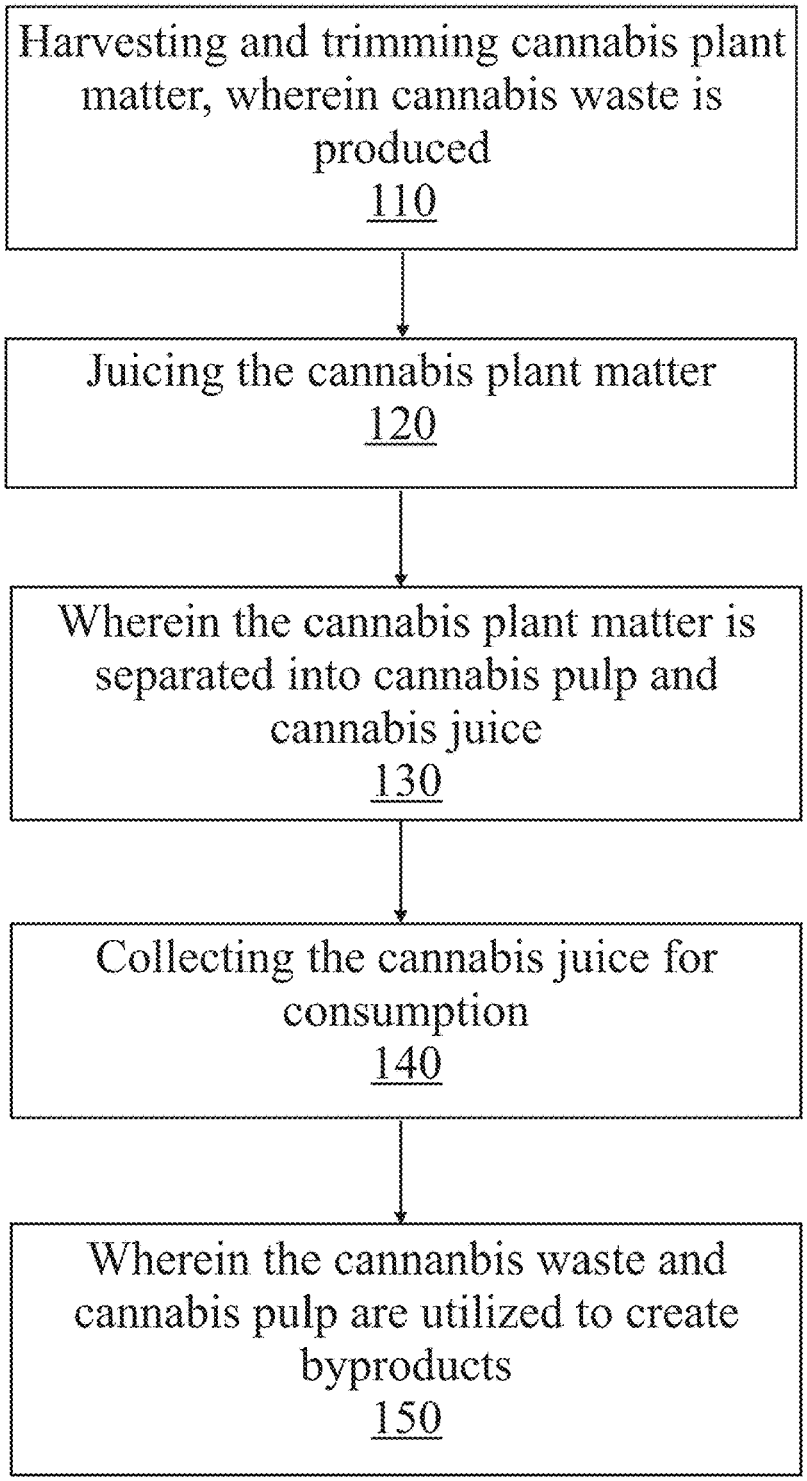
FIG. 1 is a method of processing cannabis plant matter according to an embodiment of the present invention.

FIG. 1 is a method 100 of processing cannabis plant matter according to an embodiment of the present invention. Referring now to FIG. 1, in step 110, cannabis plant matter is harvested and trimmed, producing cannabis waste as previously described. The harvesting time will be described in greater detail below. In step 120, the cannabis plant matter is juiced. In one embodiment, the juicing is via a cold press juicer, centrifugal juicer, masticating juicer, or triturating juicer. Any commercial cold-press juicer may be used, which relies on a hydraulic press, or a roller press. In one embodiment, the roller press rollers may be heated. Similarly, any portion of the cold-press juicers may be heated to help break off trichomes. This will be explained in greater detail below. Any type of juicing equipment known in the art may be used. The details of the cold-press, as well as the specific setting of the hydraulic press, such as press speed and pressure will be discussed in greater detail below. In alternative embodiments, other fruits or vegetables may be juiced with the cannabis matter in step 120, including but not limited to lemons, oranges, pineapples, grapes, mint, cucumbers, bitter blockers, or other taste changers, etc. This is a particular advantage of the present invention, as the flavor profile of the cannabis juice is improved. In step 130, the cannabis is separated into cannabis pulp and cannabis juice. In step 140, the cannabis juice is collected. In some embodiments, additional products, such as fruits, vegetables, nuts, and/or spices may be combined with the juice to improve flavors and taste, wherein the additional products are pre-processed into juice, puree, or powdered form to mix easily with the cannabis juice. The cannabis juice may be consumed to take advantages of medicinal properties of the plant, including but not limited to anti-inflammatory, neuroprotective, anti-emetic, appetite suppressant, sleep inducing and anti-proliferative properties, as well as the nutrients, essential fatty acids, aminoacids, fibers, enzymes, vitamins, and minerals.

It is a particular advantage of the present invention to utilize the cannabis pulp waste from this process. In step 150, the cannabis pulp may be utilized along cannabis waste obtained from the harvest as described above to create additional products, defined as byproducts. In one embodiment, there are a variety of means to which the byproducts are created. For instance, the cannabis pulp and/or waste may be subjected to various treatments including but not limited to drying, dehydrating, boiling, steaming, cooking, pressing, microwaving, infrared, flash freezing, freezing, blanching, frying, re-thermalizing, and centrifuging to create powder, liquid, mulch, fertilizer, solids and other forms of byproducts for re-purposing useful in a variety of purposes. In one embodiment, the variety of purposes may include but are not limited to clothing, construction materials (ie. insulation, hemperete (concrete), steel, rebar, drywall, studs, beams, flooring, windows), microchips, conducting materials, paper, biofuel, plastic composites, food additives, fertilizer, skin care products, fabric, textiles, rope, fuel, isochanvre, commercial and domestic animal feed, protein powder, dietary supplements, dietary powders, cleansing powders, and any consumables in the food and beverage sectors. In a preferred embodiment, the cannabis pulp and cannabis waste defined as cannabis process waste is dehydrated, then grinded to create a powder. Although dehydrating is the preferred method, any known method of drying may be used, including natural methods, e.g. sun drying, or machine methods, e.g. heated via a machine. In some embodiments, other methods may be utilized to create the power, including but not limited to crushing, rolling, shaking, centrifuging, smashing, etc. In some embodiments, the powder is capsuled in pill form. In other embodiments, the power is pressed into a hard pill. Yet in other embodiments, the power is liquefied using known methods to create gel caps. In some embodiments, prior to or after grinding the cannabis process waste is blanched, removing the terpenes and/or chlorophyll to improve taste for consumption. In some embodiments, the cannabis plant matter is blanched prior to the juicing method described above. The blanching details will not be described herein, and are discussed in provisional patent application 62/714,077 incorporated by reference.

Figure 2:
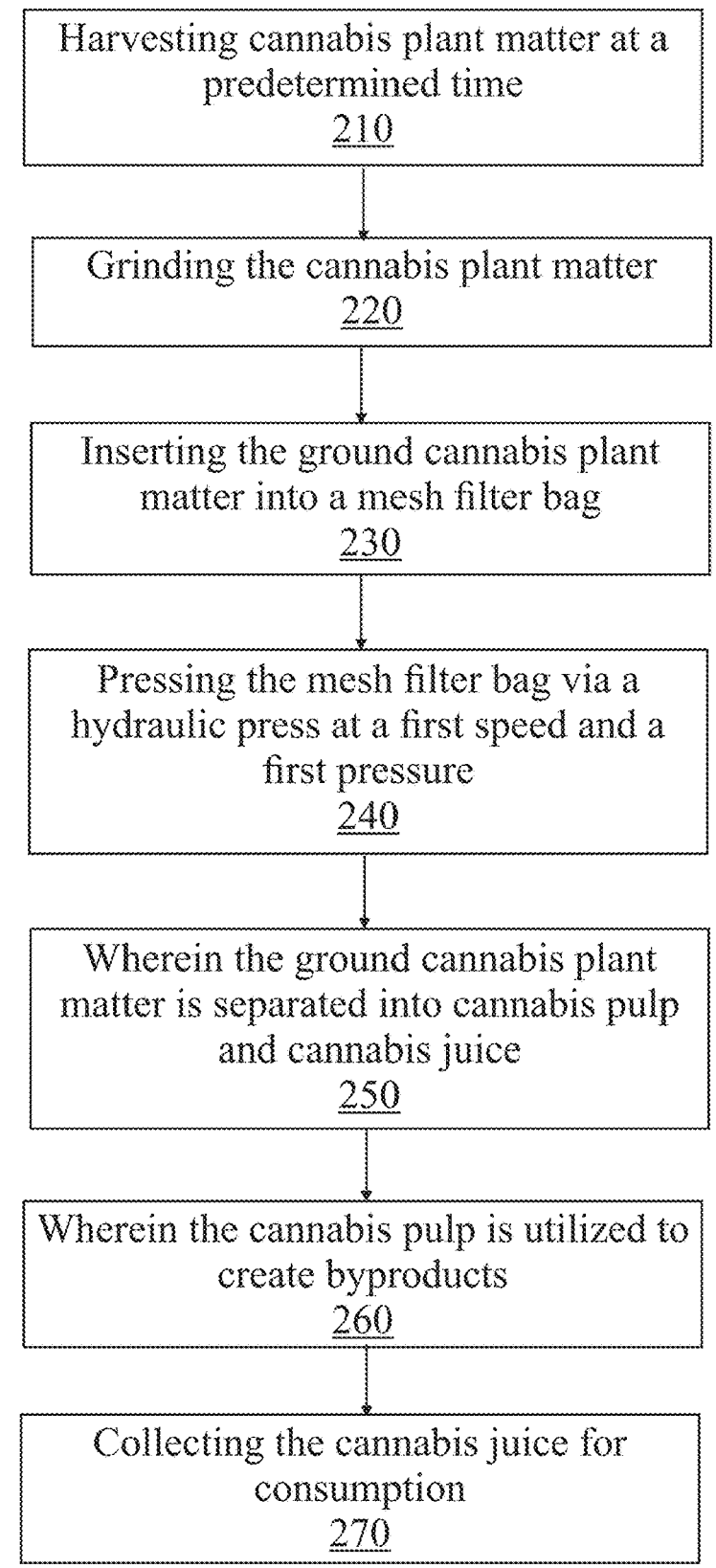
FIG. 2 is a method of processing cannabis plant matter according to an embodiment of the present invention.

FIG. 2 is a method 200 of processing cannabis plant matter according to an embodiment of the present invention. Referring now to FIG. 2, in step 210, cannabis plant matter is harvested at a predetermined time. In some embodiments, the cannabis plant matter comprises cannabis leaves and stems. Traditionally, cannabis plants are harvested exclusively for their flowers, and cannabis flowers have an ideal maturity date which varies by cannabis variety, including but not limited to *Cannabis sativa* and *Cannabis indica*. Depending on the variety, the harvesting time may be between 8 to 11 weeks. During this harvesting time, and sometimes a week or two prior, the cannabis leaves start showing signs of nutrient deficiency as the cannabis plant needs all of its available nutrients to support the cannabis flowers. In some embodiments, it is a particular advantage of the present invention to harvest the cannabis plant before the cannabis flowers form, such as in the vegetative state. This allows the whole leafy cannabis plant to be harvested without harvesting the cannabis leaves and stems separately from the flowers. Furthermore, by harvesting the entire leafy cannabis plant it reduces the amount of handling and also minimizes the amount of oxidation that occurs after harvesting, as the cannabis plant matter is exposed to air. Oxidation causes the cannabis plant matter to be subject to nutrient degradation, thus it is a goal to limit oxidation prior to processing. In the preferred embodiment, the cannabis plant matter is harvested during the vegetation stage, prior to the flowering stage allowing for the whole leafy cannabis plant to be harvested prior to flower development. The cannabis plant matter may be either from a male or female cannabis variety. Another particular advantage of harvesting the cannabis plant before the cannabis flowers form is that more cannabis plants may be grown in a shorter amount of time, as the growing cycle is reduced. This allows cannabis plant farmers to maximum crop yields, reduce the possibility of pests, insects, mites, etc. from infecting the cannabis crop. It is also critical that the harvested cannabis plant matter be free of any pesticides and be from organically grown cannabis plants. This ensures the cannabis is safe for consumption.

Still referring to FIG. 2, in step 220, the cannabis plant matter is grinded. To reiterate, the cannabis plant matter in this embodiment is the whole cannabis plant harvested in the vegetative stage as described above. The grinding allows for the maximum amount of plant matter to be processed, preferably via juicing, and more specifically increases the amount of surface area of plant matter increasing efficiency. In some embodiments, the cannabis plant matter is ground using a grinder having a blade length of ¼". This blade may be of any shape, but is preferably constructed of a circular shape. It is also critical that the grinder is attached to the juicing apparatus to limit handling to prevent possible contamination from the operators. The juicing apparatus will be discussed in greater detail below. In some embodiments, the blade is rotated at a maximum speed of 40 hertz or 2400 revolutions per min (RPM). This speed avoids heating the cannabis plant matter to a point where possible reactions may occur, including but not limited to nutrient degradation and acid cannabinoids being converting to non-acid cannabinoids which may lead to psychoactive effects for the consumer. For instance, during operation if the temperature of the cannabis plant matter reaches a temperature threshold a portion of the tetrahydrocannabinol acid (THCA) and cannabidiol acid (CBDA) may be converted into tetrahydrocannabinol (THC) and cannabidiol (CBD) respectively, i.e. decarboxylation.

In step 230, the ground cannabis plant matter is inserted into a mesh filter bag. In some embodiments, the grinder is a hopper style grinder allowing the ground cannabis plant matter to fall directly into the mesh bag. This is particularly advantageous as it reduces the handling of the fresh plant matter maintaining optimally cleanliness. The mesh filter bag comprises openings having a size of 400 to 600 microns. It should be understood that the openings are not limited to the aforementioned sizes, and optimum sizes may be discovered by routine experimentation. After pressing, which will be discussed in greater detail below, the mesh filter bag is designed to retain the pulp while allowing the juice to pass through the openings. In alternative embodiments, equivalent methods to a mesh bag may be used such as catches and trays, i.e. any method to retain the pulp. Next, in step 240, the mesh filter bag is pressed via a hydraulic press at a speed and a pressure. As previously mentioned, heating the cannabis plant matter to a point where possible reactions may occur, including but not limited to nutrient degradation and acid cannabinoids being converting to non-acid cannabinoids which may lead to psychoactive effects for the consumer is not desired. Consequently, the speed and pressure must not allow the cannabis plant matter to be heating above a threshold temperature where the possible reactions may occur. The pressure increases when the ground cannabis plant matter is actively being pressed between plates operated via the hydraulic press. The maximum pressure is 1800 pounds per square inch (PSI). Pressing at a slow speed and not exceeding the maximum pressure allows for the maximum amount of juice to be extracted without causing possible reactions.

In step 250, the ground cannabis matter is separated in cannabis pulp and cannabis juice, wherein the cannabis pulp (cannabis processing waste) may be utilized to create byproducts as previously described via step 260. In step 270, the cannabis juice is collected for consumption.

In some embodiments, decarboxylation is preferred. Therefore, the maximum pressure in step 240 above may be increased as needed, as well as the grinding speed in step 220. Further, the hydraulic plates may be heated for decarboxylation to occur. Alternatively, if desired, the cannabis juice and/or pulp may be heated for decarboxylation to occur. Likewise, the decarboxylation may occur after the cannabis processing waste has been processed into a powder.

Figure 3A:
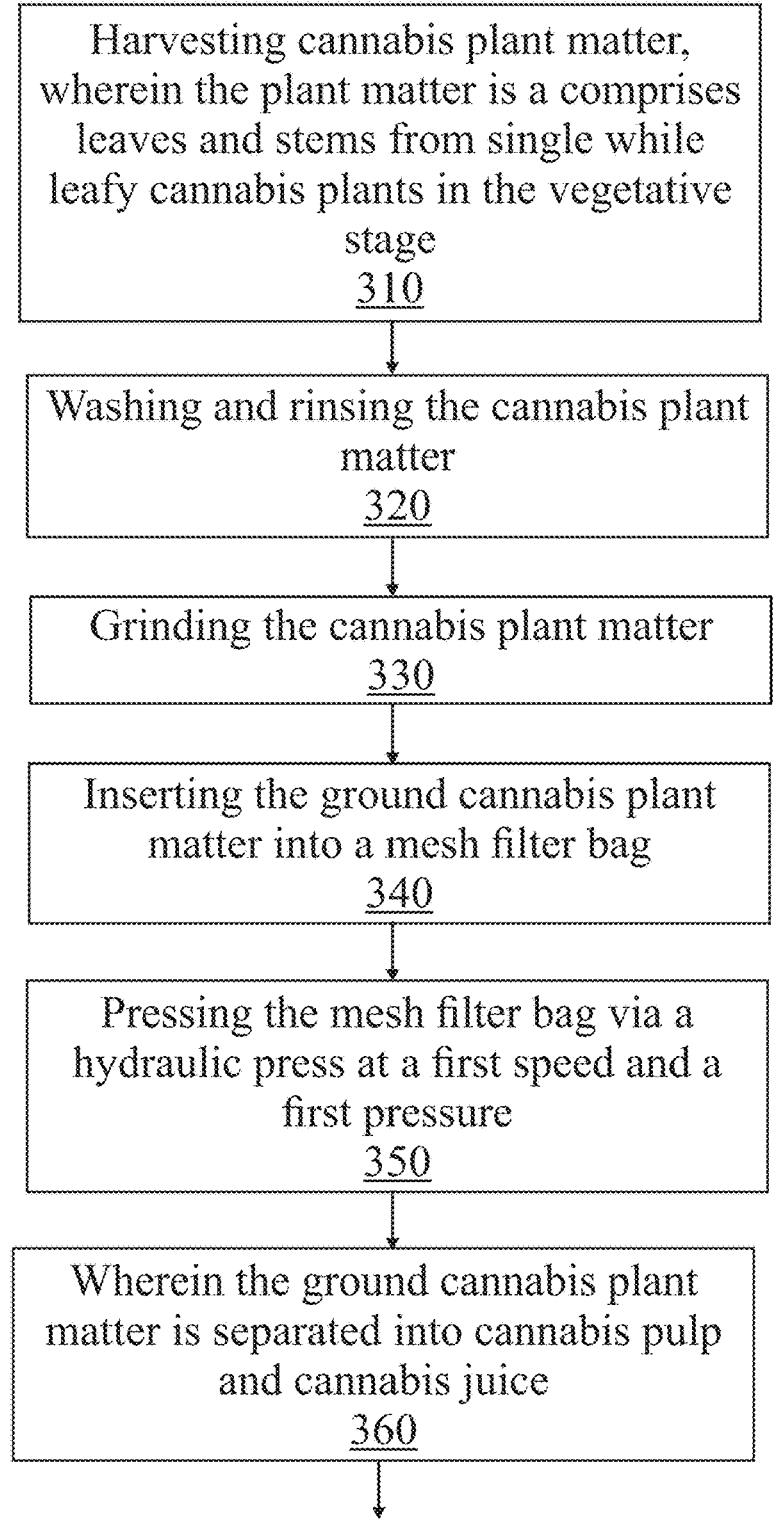
FIGS. 3A-B described a method of processing cannabis plant matter according to an embodiment of the present invention.
Figure 3B:
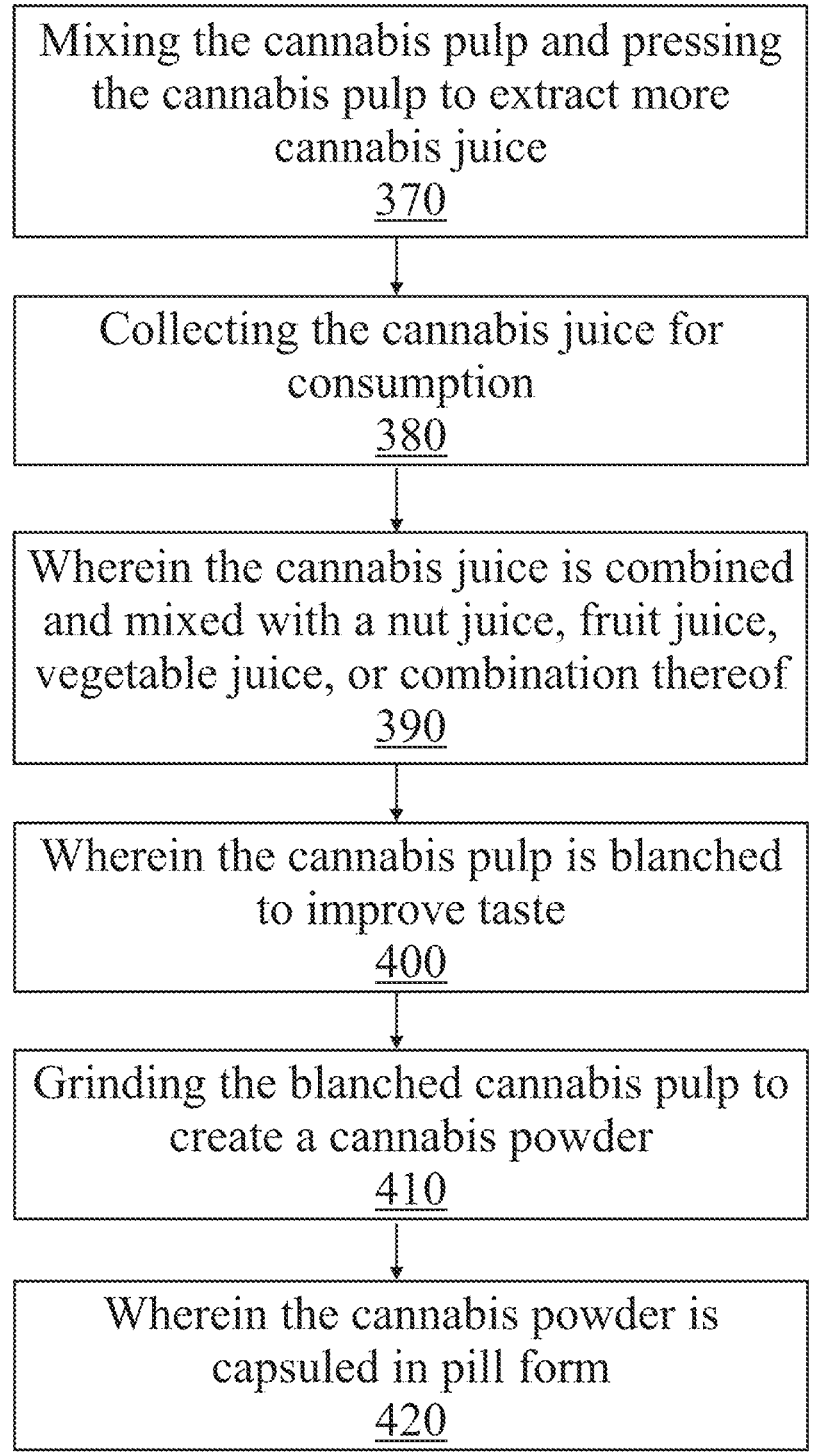

FIG. 3 is a method 300 of processing cannabis plant matter via juicing according to an embodiment of the present invention. Referring now to FIG. 3, in step 310, cannabis plant matter is harvested. In some embodiments, the cannabis plant matter comprises cannabis leaves and stems. In some embodiments, the cannabis plant matter does not include cannabis flowers and ideally the cannabis plant matter is harvested from single whole leafy cannabis plants in the vegetative stage. In step 320, the cannabis plant matter is washed and rinsed prior to juicing. This is an optional step, as the cannabis plant matter and whole leafy cannabis plants should be organically grown, however the cannabis plant matter may be washed and rinsed to remove any potential containments, bugs, dirt, and dust off prior to juicing. Next, in step 330, the cannabis plant matter is grinded. In one embodiment, the grinder is attached to the juicing apparatus to limit handling to prevent possible contamination from the operators. In other embodiments, the grinder is a separate from the juicing apparatus. In one embodiment, the grinding speed should avoid heating the cannabis plant matter to a point where possible reactions may occur, including but not limited to nutrient degradation and acid cannabinoids being converting to non-acid cannabinoids which may lead to psychoactive effects for the consumer. In other embodiments, as previously discussed, decarboxylation is desired, and various methods may be utilized to carry out the decarboxylation, including steps during the juicing or after the juicing.

In step 340, the ground cannabis plant matter is inserted into a mesh filter bag. In some embodiments, the grinder is a hopper style grinder allowing the ground cannabis plant matter to fall directly into the mesh bag. This is particularly advantageous as it reduces the handling of the fresh plant matter maintaining optimally cleanliness. It should be understood, that in alternative embodiments a mesh filter bag is not required if trays and catches are set up to catch the cannabis pulp, however a mesh filter bag is preferred. Next, in step 350, the mesh filter bag is pressed via a hydraulic press at a speed and a pressure.

In step 360, the ground cannabis matter is separated into cannabis pulp and cannabis juice. Next, in step 370, the remaining cannabis pulp is mixed in the mesh filter bag and the mesh filter bag is pressed again to extract additional cannabis juice from the cannabis pulp. Next, in step 380, the cannabis juice is collected for consumption. Although, not noted, any step and method for processing discussed herein may be included in any of the methods disclosed. For instance, in this method, fruits, vegetables, and/or nuts may be juiced with the cannabis matter or combined with the juice if already processed. It is preferred that the combination is done after processing, so that the cannabis processing waste is pure cannabis. For instance, in one embodiment, in step 390, the cannabis juice is combined with a nut juice, fruit juice, vegetable juice, or any combination thereof. However, in alternative embodiments, nut juice, fruit juice, vegetable juice, etc. may be juiced with the cannabis in step 350. Then, in step 400 the cannabis pulp (cannabis processing waste) may be utilized to create byproducts as previously described. For instance, in a preferred embodiment the cannabis pulp is blanched to improve taste. In one embodiment, the cannabis pulp is blanched in a salt, saline, and/or sodium liquid to help remove additional chlorophyll. Next, in step 410, the blanched cannabis pulp is ground to create a cannabis powder. Last, in step 420, the cannabis powder processed into pill form.

Figure 4:
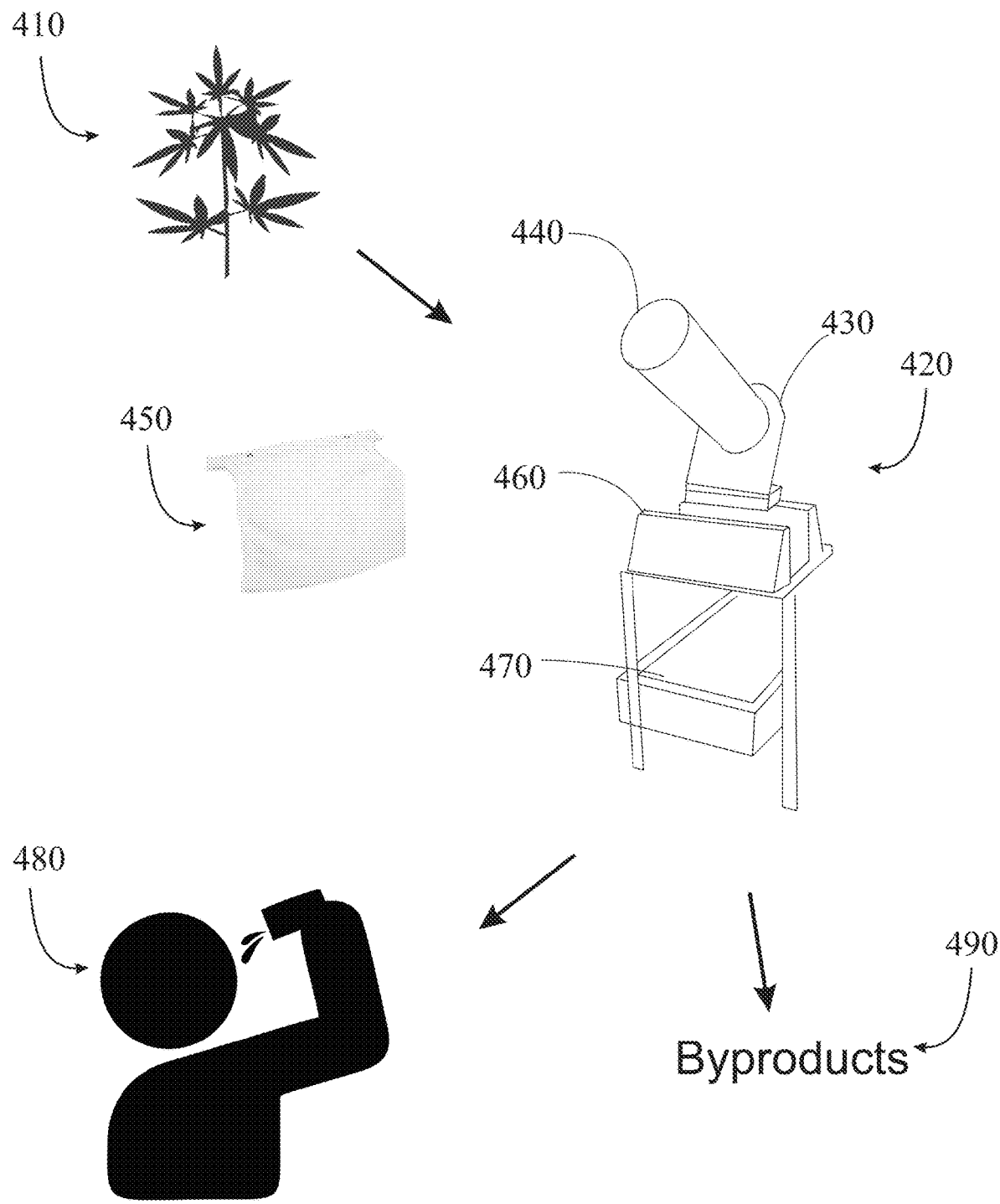
FIG. 4 is a diagram illustrating a method of processing cannabis plant matter according to an embodiment of the present invention.

FIG. 4 is a diagram illustrating a method of juicing cannabis plant matter according to an embodiment of the present invention. In some embodiments, organic leafy cannabis plants 410 are grinded by a grinder 430, wherein the grinder is attached to a hydraulic press 420. The leafy cannabis plants and corresponding plant matter are feed into a hopper 440 which guides the plant matter into the grinder at a controlled speed as well known in the art. The ground plant matter is falls directly into a mesh filter bag 450 which is located between a pair of hydraulic press plates 460. The mesh filter bag has been removed from the hydraulic press for clarity. The hydraulic press is then activated, and the pair of hydraulic press plates crushes the ground plant matter located into the mesh filter bag separating the ground plant matter into a pulp and a juice. The pulp remains in the mesh filter bag, while the juice is collected in a container 470. The cannabis juice is then ready for consumption 480. In some embodiments, the cannabis juice is mixed with other juices, including but not limited to nut, vegetable and fruit juices allowing for the cannabis juice to be more appetizing. Byproducts 490 and additional products are created from the pulp.

In some embodiments, depending on where and how the cannabis plant matter is received to carry out the methods described above, the cannabis plant matter and/or cannabis processing waste may be flash frozen, i.e. frozen rapidly to prevent the formation of ice crystals on the cannabis plant matter. In other embodiments, the cannabis plant matter and/or cannabis processing waste may be frozen. The flash frozen or frozen cannabis is then processed via the methods described above.

In some embodiments, the cannabis waste, and particularly the cannabis powder created from the cannabis pulp, or just the cannabis pulp, is mixed back into the cannabis juice, such that the cannabis juice includes cannabinoids from the pulp. As it was indicated previously, the cannabis juice actually doesn't contain the amount of cannabinoids as expected, since the cannabinoids are retained in the pulp. In some embodiments, a portion of the pulp powder is mixed back into the juice. In other embodiments, a portion of the pulp powder is mixed back into any cannabis juice, including cannabis juice obtained from a different method than disclosed above. In some embodiments, any cannabis substance that has a high cannabinoid content cannabis, such as cannabis isolates, oils, synthetic, powders, etc. are mixed with the cannabis juice. In some embodiments, the cannabis pulp powder is reduced to nano size, such that the cannabis pulp powder contains particles of nano size, such as less than 200 or 100 micrometers. The nano size improves the bioavailability of the cannabinoids, and improves the ability of the pulp powder to be properly mixed and dissolved into the cannabis juice. In one embodiment, ball milling is the preferred method to reduce the cannabis pulp to nano size. More information related to reducing to nano size can be found in Applicant's co-pending application Ser. No. 16/388,821 hereby incorporated in its entirety at least by reference. Further, in some embodiments, the nano sized cannabis pulp powder is encapsulated into a liposome or micelles. More information related to encapsulating the nano sized cannabis pulp powder can be found in Applicant's co-pending application Ser. No. 16/439,706 hereby incorporated in its entirety at least by reference.

In some embodiments, the cannabis juice is dehydrated by any known dehydration method, such as freeze-drying, and then processed into a powder. Then in some embodiments, the pulp from previous methods, such as pulp powder, may be added to the cannabis juice dehydrated powder to supplement the powder makings to increase the cannabinoid content of the original powder.

In some embodiments, processes are being performed prior to the juicing of the cannabis plant matter. In one embodiment, if the cannabis plant matter is dried, a method step of hydrating the dried cannabis plant matter prior to juicing is provided. As well known in the art a filter or mesh screen is used in the juicing process to retain the cannabis pulp from entering the juice. In one embodiment, the cannabis plant matter is reduced to smaller than the mesh or filter size. Thus after pressing, portions of the cannabis pulp containing cannabinoids will pass through the filter or mesh screen. If the reduced cannabis is dried, a further step of hydrating the reduced cannabis plant matter may be provided. In one embodiment, the reduced cannabis contains nano sized particles.

In one embodiment, the cannabis juice obtained from the methods discussed above can be the liquid used to rehydrate any cannabis plant matter, such as previously reduced cannabis plant matter, in further steps, wherein the rehydrated cannabis plant matter can be subjected to cold pressing such that a concentrated liquid can be provided.

In some embodiments, as previously mentioned the cannabis plant matter may be subjected to additional rounds of pressing. It is advantageous, to adjust, agitate, reposition the cannabis plant matter between rounds of pressing to maximum the cannabinoids that enter the cannabis juice. In some embodiments, the cannabis plant matter that has already been pressed is rehydrated with fresh water or the cannabis juice provided by the first or earlier pressing process. In some embodiments, the process of adjusting, agitating, or repositioning includes blending or grinding the cannabis plant matter with or without liquid (fresh water or cannabis juice) prior to repressing. This process can be repeated until desired amount of cannabinoids are into the juice. In some embodiments, the juice is dehydrated and processed into a powder. In some embodiments, a cannabis pulp and cannabis juice mixture is dehydrated and processed into a powder. In some embodiments, the cannabis pulp is dehydrated and processed into a powder. The powder can then be added and processed to any previous steps discussed herein, including but not limited to encapsulation, emulsification, sonication, infusion, such as oils, beverages, fluids, or building materials.

In some embodiments, the cannabis plant matter can be frozen prior to processing. In some embodiments, the frozen cannabis plant matter can be ground into freezing slurry then subjected to cold pressing. Any previously steps can then be applied. Similarly, freezing water or liquid can be added to cannabis plant matter to create a slurry/paste/mud that is then subjected to cold-pressing. Freezing the cannabis in a liquid (or gas) helps break off the trichomes and frees them up to move into the juice at a higher concentration. For the purpose of the disclosure freezing includes cold temperatures around freezing 50 degrees or lower. The gas may be $CO_2$ (supercritical), nitrogen, methane, ozone, or similar gas. As previously mentioned, components of the actual cold-press juicer may be heated to also assist in breaking off trichomes during the juicing process. Similarly, components of the actual cold-press juicer may be cooled to aid in this process.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention. For instance, the methods described above may be modified for commercial applications and utilize bath processing, or continuous flow processing methods.

In addition, reference to "first," "second," "third," and etc. members throughout the disclosure (and in particular, claims) are not used to show a serial or numerical limitation but instead are used to distinguish or identify the various members of the group.

What is claimed is:

1. A method of making cannabis juice enriched with cannabinoids comprising:
   (a) freezing cannabis;
   (b) thawing the frozen cannabis;
   (c) juicing the thawed cannabis via a cold-press juicer, wherein the cold-press juicer separates the thawed cannabis into cannabis juice and cannabis pulp;
   (d) collecting the cannabis juice and the cannabis pulp;
   (e) drying the cannabis pulp;
   (f) processing the cannabis pulp into a powder;
   (g) using the cannabis pulp powder for a different use; and
   (h) mixing in a different cannabis with the cannabis juice to enrich the cannabis juice with cannabinoids.

* * * * *